(12) United States Patent
Bevinakatti et al.

(10) Patent No.: US 9,023,329 B2
(45) Date of Patent: May 5, 2015

(54) STRUCTURANTS FOR OIL PHASES

(75) Inventors: Hanamanthsa Shankarsa Bevinakatti, Ingleby Barwick (GB); Alan Geoffrey Waite, Darlington (GB); Thomas Phillip Wells, London (GB)

(73) Assignee: Croda International, PLC, Goole, East Yorkshire (GB)

( * ) Notice: Subject to any disclaimer, the term of this patent is extended or adjusted under 35 U.S.C. 154(b) by 988 days.

(21) Appl. No.: 12/086,985

(22) PCT Filed: Dec. 21, 2006

(86) PCT No.: PCT/GB2006/004831
§ 371 (c)(1),
(2), (4) Date: Mar. 17, 2010

(87) PCT Pub. No.: WO2007/074331
PCT Pub. Date: Jul. 5, 2007

(65) Prior Publication Data
US 2010/0183534 A1    Jul. 22, 2010

(30) Foreign Application Priority Data
Dec. 24, 2005 (GB) .................................. 0526455.1

(51) Int. Cl.
| | | |
|---|---|---|
| A61Q 15/00 | (2006.01) | |
| A61Q 17/04 | (2006.01) | |
| A61Q 19/00 | (2006.01) | |
| A61K 8/85 | (2006.01) | |
| A61K 8/02 | (2006.01) | |
| A61Q 1/02 | (2006.01) | |
| A61Q 1/04 | (2006.01) | |
| A61Q 1/06 | (2006.01) | |
| A61Q 1/10 | (2006.01) | |
| A61Q 1/14 | (2006.01) | |
| A61Q 5/02 | (2006.01) | |

(52) U.S. Cl.
CPC ................ *A61K 8/85* (2013.01); *A61K 8/0229* (2013.01); *A61Q 1/02* (2013.01); *A61Q 1/04* (2013.01); *A61Q 1/06* (2013.01); *A61Q 1/10* (2013.01); *A61Q 1/14* (2013.01); *A61Q 5/02* (2013.01); *A61Q 15/00* (2013.01); *A61Q 17/04* (2013.01); *A61Q 19/00* (2013.01)

(58) Field of Classification Search
CPC ........ A61Q 15/00; A61Q 17/04; A61Q 19/00; A61Q 1/02; A61Q 1/04; A61Q 1/06; A61Q 1/10; A61Q 1/14; A61Q 5/02
See application file for complete search history.

(56) References Cited

U.S. PATENT DOCUMENTS

| | | | |
|---|---|---|---|
| 6,555,097 B1 | 4/2003 | Rabe et al. | |
| 7,317,068 B2 * | 1/2008 | Burgo | ............................ 528/272 |
| 2005/0287103 A1 * | 12/2005 | Filippi et al. | ................ 424/70.22 |
| 2006/0019848 A1 | 1/2006 | Luo et al. | |
| 2010/0047194 A1 * | 2/2010 | Bevinakatti et al. | ............. 424/59 |

FOREIGN PATENT DOCUMENTS

| | | |
|---|---|---|
| EP | 0132293 | 1/1985 |
| JP | 56012340 | 2/1981 |
| WO | WO 97/17059 | 5/1997 |
| WO | WO 01/00172 | 1/2001 |
| WO | WO 02/47620 | 6/2002 |
| WO | WO 2004/041150 | 5/2004 |

OTHER PUBLICATIONS

International Search Report dated May 31, 2007 for PCT/GB2006/004831.
Examination Report mailed Jul. 7, 2014 in corresponding Taiwanese application (no English translation currently available).

* cited by examiner

*Primary Examiner* — Aradhana Sasan
(74) *Attorney, Agent, or Firm* — Jones Day

(57) ABSTRACT

Polyester oil structurants are obtainable by the reaction of a $C_4$ to $C_{10}$ Q dicarboxylic acid, a polyol and a $C_{16}$ to $C_{30}$, particularly a $C_{20}$ to $C_{24}$, monocarboxylic fatty acid. The structurants can be used to provide structure, particularly thickening and/or gelling, in oils of a wide range of polarity. Thickened oils can find application in a range of personal care and other applications.

23 Claims, No Drawings

STRUCTURANTS FOR OIL PHASES

This invention relates to structurants for oil phases, particularly to oil structurants which are oligoester reaction products of polyols, $C_4$ to $C_{10}$ dicarboxylic acids and long chain monocarboxylic fatty acids, to oil phases including them and to the use of such structured oil phases particularly in personal care products such as cosmetics.

Oils possess highly desirable cosmetic characteristics, such as cleansing, make-up removal, and emolliency, but their fluid form makes them inconvenient to use and/or makes their application difficult and sometimes unpleasant. Such disadvantages can be reduced by using the oil in the form of a structured or particularly a thickened composition, such as a cream or a gel or in the form of an emulsion, particularly a water in oil emulsion, where thickening is only needed for the continuous oily phase. Thickening the oily phase is also done to prepare cosmetic gels, particularly anhydrous gels which are useful, particularly where substances in the composition are sensitive to moisture and/or to oxygen.

Materials that are available for oil structuring, thickening or gelling include waxes, silicas, such as fumed silica, hydrophobically modified clays such as bentonites, fatty acid metal salts, such as aluminium magnesium hydroxide stearate, hydroxyfatty acid esters, such as trihydroxystearin (solid hydrogenated castor oil), or oligosaccharide ester derivatives such as dextrin palmitate. While they can be effective structurants, gelling agents and thickeners, these materials do have disadvantages. For example, waxes can give the end products an undesirable skin feel and may reduce the gloss of products, very disadvantageous for lipsticks, and other personal care products; hydrophobically modified clays and aluminium magnesium hydroxide stearate structured oils do not spontaneously emulsify on dilution with water, and hydrophobically modified clays have high mixing energy requirements, trihydroxystearin and high molecular weight polymers generally require the use of high processing temperatures e.g. up to 90° C., in making structured oils, silicas have low bulk density, and dextrin palmitates are very expensive.

The present invention is based on our finding that ester products obtainable by reaction of polyols, $C_4$ to $C_{10}$ dicarboxylic acids and long chain monocarboxylic fatty acids and in particular such products that have multiple pendent fatty acid groups usually also with free hydroxyl groups, can be very effective structurants in oil phase systems.

The present invention accordingly provides a polyester oil structurant compound which is obtainable by the reaction of a $C_4$ to $C_{10}$ dicarboxylic acid, a polyol and a $C_{16}$ to $C_{30}$, particularly a $C_{20}$ to $C_{24}$, monocarboxylic fatty acid.

In particular the invention includes a fatty acid polyester oil structurant compound which is obtainable by the reaction of a $C_4$ to $C_{10}$ dicarboxylic acid, a polyol, having an average of from 1 to 2 primary hydroxyl groups and at least one, particularly 1 to 4, secondary hydroxyl group(s) and a $C_{16}$ to $C_{30}$, particularly a $C_{20}$ to $C_{24}$, monocarboxylic fatty acid.

The invention further specifically includes a fatty acid polyester oil structurant compound which is obtainable by the reaction of a $C_4$ to $C_{10}$ dicarboxylic acid, a polyol selected from glycerol, sorbitol, sorbitan and mixtures or combinations of these, and a $C_{16}$ to $C_{30}$, particularly a $C_{20}$ to $C_{24}$, monocarboxylic fatty acid.

The compounds of the present invention are designed for use as oil structurants, particularly thickeners and/or gellants, and the invention accordingly includes a structured oil system which includes as an oil phase structurant a compound which is a polyester compound which is obtainable by the reaction of a $C_4$ to $C_{10}$ dicarboxylic acid, a polyol and a $C_{16}$ to $C_{30}$, particularly a $C_{20}$ to $C_{24}$, monocarboxylic fatty acid.

The compounds of the invention find particular use as structurants in oil based or oil containing personal care formulations and the invention accordingly includes a personal care product or formulation which includes a thickened oil system which includes as a structurant a polyester compound which is obtainable by the reaction of a $C_4$ to $C_{10}$ dicarboxylic acid, a polyol, which desirably has an average of form 1 to 2 primary hydroxyl groups and at least one, particularly 1 to 4, secondary hydroxyl group(s) and particularly is selected from glycerol, sorbitol, sorbitan and mixtures or combinations of these, and a $C_{16}$ to $C_{30}$, particularly a $C_{20}$ to $C_{24}$, monocarboxylic fatty acid.

Additionally the invention includes the use of the compounds of the invention as oil structurants, in particular in personal care products or formulations.

In referring to compounds of and used in this invention as "polyesters" or "oligoesters", we are referring to the multiple ester linkages in the compounds—derived from reaction between the polyol and the di- and mono-carboxylic acids. They do not necessarily imply that the compounds have polyester chains—of alternating dicarboxylic acid and polyol, although such chains are a desirable feature of many compounds of and used in the invention.

The term "structurant" refers to the provision of effects ranging from increasing the viscosity (viscosifying or thickening) to gelling the oil (creating a three dimensional structure at the molecular level which "traps" the continuous phase oil) and includes the possibility of generating liquid crystal like phases in the oil, all of which can enhance the stability of dispersed phases in the oil.

The polyol used as a starting material in making the polyesters of the invention groups typically have at least 3 and up to 8 hydroxyl groups and desirably has an average of from 1 to 2 primary hydroxyl groups and at least one, particularly 1 to 4, secondary hydroxyl group(s). They can be considered as being of the formula (I): $R^1$—$(OH)_n$, where n is from 3 to 8 and particularly from 3 to 6. The group $R^1$ is desirably aliphatic hydrocarbyl, usually saturated, having from 3 to 10 and particularly 3 to 8, and especially 3 to 6, carbon atoms and will usually be linear though it may include branching. In the polyol (I) there will generally be one or two primary hydroxyl groups (on the polyol terminal carbon atoms) and at least one and commonly n-2 secondary hydroxyl groups.

Desirably, the polyol (I) is of the formula (Ia): $HOH_2C$—$(CHOH)_p$—$CH_2OH$ where p is from 1 to 6, more usually from 1 to 4. Suitable polyols include glycerol, $C_4$ polyols such as threitol and erythritol, $C_5$ polyols such as inositol, arabitol and xylitol and $C_6$ polyols such as sorbitol, and derived materials such as sorbitan. The $C_4$ to $C_6$ polyols are commonly the reduced or hydrogenated forms of corresponding tetrose, pentose and hexose sugars. Desirably the polyol is glycerol, and especially sorbitol and sorbitan (usually derived in situ from sorbitol) or a mixture or combination of these.

It is possible to include relatively small proportions of residues derived from diols e.g. as derived from ethylene, diethylene, triethylene or propylene glycols or isosorbide (derived by di-anhydridisation of sorbitol). The inclusion of such diol residues may enable adjustment of properties of the polymers, however, the proportion of such residues will generally be low, typically an average of not more than 20 mol %, more usually not more than 15 mol %, and desirably not more than 10 mol % e.g. from 1 to 10 mol %, and particularly from 1 to 5 mol % of the polyol residues in the compounds.

Especially where the polyol has four or more carbon atoms and four or more hydroxyl groups usually two primary hydroxyls and 2 or more secondary hydroxyls, and in particular where the polyol is of the formula (Ia) with p being 3 or 4, it may be susceptible to react by an intramolecular etherification (anhydridisation) reaction to form cyclic ethers. For example sorbitol can form sorbitan cyclic ethers which may react further to form the dicydic diether iso-sorbide, reducing the number of hydroxyl groups available for esterification. When sorbitan residues are desired in the product, it will usually be done by, in effect, in situ formation of the sorbitan; and correspondingly it is likely that some sorbitol will be converted into sorbitan when trying to make sorbitol esters. Although anhydridisation will occur its extent may be controlled (at least to a limited extent) by selection of the reaction conditions e.g. use of acidic catalysts, particularly if linked with higher reaction temperatures, will lead to a greater degree of anhydridisation than the use of alkaline catalysts (and lower reaction temperatures will lead to a lower degree of anhydridisation).

The dicarboxylic acid used as a starting material in making the polyesters of the invention have from 4 to 10 carbon atoms and will usually be aliphatic compounds. Typically, the dicarboxylic acid is of the formula (II): HOOC—$R^2$—COOH, where $R^2$ is a $C_2$ to $C_8$ hydrocarbyl group which can be saturated or unsaturated, linear or branched and can be aromatic e.g. a phenyl ring (thus giving a phthallc, terephthalic or iso-phthalic dicarboxylic acid) or and desirably aliphatic, typically an alkylene or alkenylene group, and may be cyclic though it is desirably open chain. Commonly $R^2$ is a group: —$(CH_2)_m$—, where m is from 2 to 8. Because mixtures of different dicarboxylic acids (or reactive derivatives) may be used to make materials used in practice, m may appear to be non integral, because it will be an average. Suitable reactive derivatives of the dicarboxylic acids include lower e.g. $C_1$ to $C_4$ and particularly methyl, alkyl esters (usually diesters) and anhydrides, particularly cyclic anhydrides such as succinic, maleic and phthalic anhydrides.

The monocarboxylic acid used as a starting material in making the polyesters of the invention are $C_{16}$ to $C_{30}$, particularly $C_{18}$ to $C_{30}$ and desirably $C_{20}$ to $C_{24}$ hydrocarbyl, particularly aliphatic and especially saturated, linear aliphatic fatty acids. Typically they are of the formula (III): $R^5CO_2H$, where $R^5$ is long chain aliphatic hydrocarbyl group, specifically a $C_{15}$ to $C_{29}$, usually a $C_{17}$ to $C_{29}$, particularly a $C_{19}$ to $C_{23}$, hydrocarbyl, particularly alkyl, group. Reactive derivatives of monocarboxylic acids that can be used in the synthetic reaction include lower e.g. $C_1$ to $C_4$ and particularly methyl, alkyl esters.

The length of the monocarboxylic fatty acid chains appears to be directly related to the structuring effectiveness of compounds of and used in the invention—the use of shorter chain fatty acids than $C_{16}$ appears to give little if any structuring e.g. thickening, viscosifying or gelling effect (at least at ambient temperature) and we have found that longer chains e.g. $C_{18}$ or particularly $C_{20}$ or longer chains can give more effective structurants. Thus, desired monocarboxylic acids are stearic and especially, behenic acid. The presence of branching or unsaturation in the chains of the monocarboxylic acids is generally undesirable as it makes products based on such acids much less effective structuring agents.

Mixtures of monocarboxylic acids may be used if desired and it may be advantageous in permitting the properties of the products to be adjusted. Using combinations of long chain monocarboxylic acids will generally give products whose properties are intermediate between the properties of the respective products made wholly with the respective fatty acids. Including small proportions of short chain (particularly shorter than 16 carbon atoms) or branched or unsaturated monocarboxylic acids (of any chain length) will tend to make the products less likely to be gellant type structurants. The proportions of short chain or branched or unsaturated monocarboxylic acids will generally be low, typically an average of not more than 30 mol %, more usually not more than 25 mol %, and desirably not more than 20 mol % e.g. from 1 to 20 mol %, and particularly from 5 to 15 mol % of the total moncarboxylic fatty acid residues in the compounds.

Significant thickening can be achieved with even relatively small polyester molecules and the compounds of and used in the invention typically have a number average molecular weight of from 1000 to 10000, more usually from 1200 to 7000, and particularly from 1300 to 6000 and a corresponding weight average molecular weight of from 2500 to 20000, more usually from 2500 to 12000, and particularly from 2500 to 10000. (Based on molecular weights measured by gel permeation chromatography against polystyrene standards.) Such molecular weight values correspond to chain lengths derived from the nominal polymerisation esterification of the polyol and the dicarboxylic acid of from about 1 to about 20, more usually from about 1 to about 10 and particularly from about 1 to about 7.5, repeat units (based on a hydroxy/carboxy ended polyol-dicarboxylic acid ester unit). Of course, the number of "repeat units" and molecular weight are average values and may thus be non-integral.

The extent to which the total available hydroxyl groups in the reaction components used in making the products of the invention are esterified can have a significant effect on the efficiency of the compounds of and used in the present invention as structurants. Generally a minimum of 40%, more usually at least 45% and desirably at least 50% of the total polyol hydroxyl groups will be esterified. At lower levels of esterification, the proportion of free hydroxyl groups is sufficiently high to significantly reduce the oil solubility of the oligoesters and thus to have a detrimental effect on the thickening performance of the compounds. Clearly the maximum number of such ester residues will depend on the number of hydroxyl groups in the original polyol. However, in practice it is difficult to achieve complete reaction so the level of esterification is usually not more than about 90%, e.g. up to about 80% of the hydroxyl groups in the original polyol. (In reckoning the number of hydroxyl groups in the original polyol, any that react to form ethers under the reaction conditions e.g. as in forming sorbitol from sorbitan, are not included.) Within these ranges, the proportion of free hydroxyl groups may be used to modulate or moderate the thickening effects of the compounds.

In order to generate a preponderance of hydroxyl (over carboxyl) ends in the product oligoester, the polyol will generally be used in molar excess over the dicarboxylic acid, most commonly at a molar ratio of polyol:diacid of from 1.1 to 2, more usually from 1.25 to 2. The amount of the monocarboxylic acid used will depend on the number of hydroxyl groups in the polyol and the proportion of hydroxyls that it is desired to esterify in the product. Generally the proportion used will be from 1 to 2.5, more usually from 1 to 2.2, and especially from 1.2 to 2, moles monocarboxylic acid per mole of polyol. Accordingly, the ratios of the polyol, dicarboxylic acid and monocarboxylic acid used will generally be in the range 1:0.5 to 0.95:1 to 2.5, more usually 1:0.5 to 0.85:1 to 2.2, and desirably 1:0.6 to 0.85:1.2 to 2. The products of the invention typically have a hydroxyl number (OH no, in mg(KOH).g$^{-1}$) of at least 15 and commonly up to 50 though higher values are possible for example up to about 250, more usually from 50, particularly 60, to 220. The higher values can be achieved by deliberately using a highly hydroxylic polyol, such as sorbitol, as starting material, and carrying out the synthesis so as to minimise loss of free hydroxyl groups e.g. avoiding cylclising etherification synthetic side reactions by using non-acid, especially alkali, catalysts, at relatively high levels (see below). One effect arising from the higher free OH content of such materials is that the products have higher melting points than otherwise similar products having lower OH values and this may be advantageous in end use formulations such as lipstick. Thus, generally compounds of the invention are solids with melting points of from 50 to 70° C., though compounds having higher OH values particularly over 100, the melting point can be up to 85° C.

(As directly measured the OH no includes both hydroxylic and carboxylic OH groups, the contribution from hydroxylic OH groups can be obtained by subtracting the Acid Value from the OH no—both measured in $mg(KOH).g^{-1}$—to give a value which can be described as the "free OH no".)

The compounds of and used in the invention are oligo- or poly-esters of the polyol, dicarboxylic acid and monocarboxylic acid, but their exact molecular structure is unclear. From molecular weight measurements using gel permeation chromatography it appears that the polyol and dicarboxylic acid are linked to form an oligo- or poly-meric skeleton and that the monocarboxylic acid is esterified to some or all of the remaining polyol hydroxyl groups. It is probable that the compounds are mixtures of different molecules and are likely to include some relatively straight linear chains e.g. as from reaction between the dicarboxylic acid and am-primary hydroxyl groups as in glycerol or sorbitol, some "kinked" chains such as arising from reaction between the dicarboxylic acid and non terminal, particularly secondary, hydroxyl groups, and some branched or even crosslinked chains or groups.

The compounds of and used in the invention are mainly OH ended and the proportion of free carboxylic acid groups is small, as reflected in the measured acid values which typically corresponding to a significantly higher equivalent weight for the carboxylic acid content than the measured molecular weight. Typically acid values will commonly be less than 10, e.g. less than 5, $mg(KOH).g^{-1}$ though where the polyol is susceptible to anhydridisation e.g. sorbitol, and the product is desired to have low levels of anhydridisation, less driving conditions may be used in the esterification and this may result in somewhat higher acid values e.g. up to 20 $mg(KOH).g^{-1}$. Reflecting that the products of and used in the invention are mainly OH ended (rather than carboxyl ended) the OH no, and desirably the free OH no, will typically be significantly higher than the acid value (both measured in $mg(KOH).g^{-1}$).

The compounds of and used in the invention can be made by a generally conventional esterification using a polyol, a dicarboxylic acid (or a reactive derivative) and a monocarboxylic acid (or a reactive derivative) as starting materials. We have successfully made the compounds of and used in the invention by a direct one stage route in which all three components: the polyol, the dicarboxylic acid (or reactive derivative) and the monocarboxylic acid (or reactive derivative) are mixed and reacted together under (trans-)esterification conditions, particularly at elevated temperatures and in the presence of a catalyst.

The reaction conditions will typically involve using a reaction temperatures of from 150 to 250° C., and particularly 170 to 240° C. Where free acids are used as reagents in direct esterification, the reaction may be carried out under atmospheric pressure or under moderate vacuum e.g. at pressures from 50 to 250 mBar, particularly about 100 mBar gauge to facilitate removal of water of reaction, and trans-esterification reactions using lower alkyl esters will usually be carried out at ambient pressure.

Suitable catalysts will depend on the actual starting materials and the desired product. For direct esterifications typical catalysts include basic catalysts such as alkali metal hydroxides or carbonates, such as sodium or potassium hydroxide or carbonate, particularly potassium carbonate; or acidic catalysts, such as sulphonic acids e.g. p-toluene sulphonic acid or phosphorus oxyacids such as phosphoric acid, or, particularly if it is desirable to avoid colour forming oxidation reactions, especially with starting polyols such as sorbitol, phosphorous acid, and catalysts combining phosphoric and/or phosphorous acid with alkali, typically at a molar ratio of from 1:1 to 1:3; and for trans-esterifications typical catalysts include relatively mild alkali metal base such as carbonates, particularly potassium carbonate, titanate esters, such as tetrabutyl titanate.

The amount of catalyst used will be chosen to achieve the desired level of catalysis and will usually be within the range from 0.5 to 20% by weight based on the weight of polyol used. Typically, the amount of catalyst will be from 0.75 to 10% by weight based on the polyol. Where it is desired to avoid side reactions such as cycling etherification when using highly hydroxylic polyols like sorbitol, especially where it is desired to produce products having particularly high hydroxyl values, then higher level of esterification catalyst e.g. up to 20%, particularly about 15%, by weight based on the polyol may be used to increase preference for the desired reaction, and catalytic materials that promote cyclisation such as acids, will generally be avoided.

The invention further includes a method of making a structurant compound of the invention which comprises reacting a polyol (or reactive derivative), a dicarboxylic acid (or reactive derivative) and a fatty monocarboxylic acid (or reactive derivative) together under esterification conditions to form a fatty polyester structurant derivative.

A wide range of oils can be structured using the compounds of the invention and the best such compounds will provide structuring in a wide range of oils (rather than a relatively narrow range for each structuring compound). The range of oil polarity for which structuring can be provided is wide ranging from non-polar oils such as paraffinic oils to alkoxylate oils. One way of expressing this range of polarity is to use a numeric solubility parameter. We have found that Hansen and Beerbower solubility $\delta^t$ parameter combining dispersive (van der Waals), polar (Coulombic) and hydrogen bonding component (see the CRC Handbook of Solubility Parameters and Other Cohesion Parameters pp 85 to 87) provide good correspondence with the polarity as reflected in the performance of the oils that we have investigated. The numerical values of solubility parameter given below are Hansen and Beerbower $\delta^t$ values abbreviated as "HBSP" values. Generally structurants of and used in this invention can provide structure in oils with HBSP values ranging from 15 (very non-polar) to 25 (highly polar) particularly from 15 to 22.

Typical oils that can be structured using compounds of the invention include:

fatty alcohol polyalkoxylate, particularly propoxylates such as the alkoxylates of $C_{12}$ to $C_{20}$ fatty, particularly $C_{14}$, $C_{16}$ and $C_{18}$ fatty alcohols which can be linear e.g. as in palmitic and stearic acids, or branched e.g. as in isostearyl alcohol (in practice a product typically derived from dimer acid manufacture which contains a mixture of mainly branched $C_{14}$ to $C_{22}$ alcohols averaging about $C_{18}$), with from 3 to 25 particularly from 7 to 20 alkoxylate alkoxylate, especially ethoxylate, propoxylate or mixtures of ethoxylate and propoxylate, units e.g. the stearyl alcohol 15-polypropoxylate—ARLAMOL E (HBSP 20.8) ex UNIQEMA;

ester oils particularly those based on $C_2$ to $C_{22}$ linear, branched or unsaturated fatty acids and linear, branched or unsaturated fatty alcohols, and typically esters derived from monocarboxylic acid(s) with monohydric alcohol(s); di- or tri-carboxylic acid(s) with monohydroxy alcohol(s) acid with monohydric alcohol(s); or di- or poly-hydric alcohol(s) with monocarboxylic acid(s). Examples include ESTOL 3609 (HBSP 20.4) ex UNIQEMA, isopropyl isostearate—PRISORINE 2021 (HBSP 17.7) ex UNIQEMA and methyl oleate—PRIOLUBE 1400 (HBSP 17.9) ex UNIQEMA. Particularly where the end use formulation is for stick formulations e.g. cosmetics like lipsticks, relatively long chain polyhydric alcohol esters such as trimethylolpropane triisostearate—PRISORINE 3630 ex UNIQEMA, castor oil {non-hydrogenated—hydrogenated castor oil (trihydroxystearin) is a solid used as a thickener}, glycerol triisostearate—PRISORINE 2041 ex UNIQEMA, pentaerythritol tetraisostearate—PRISORINE 3631 ex UNIQEMA—and other similar relatively viscous liquid ester oils;

aromatic ester oils, particularly esters of benzoic acid and $C_8$ to $C_{18}$ monohydric alcohol(s) e.g. FINSOLVE TN (HBSP 19.1) a $C_{12}$ to $C_{15}$ benzoate oil ex FINETEX;

branched liquid fatty alcohols, particularly Guerbet alcohols e.g. octyldodecanol or isostearyl alcohol (see above) e.g. isostearyl alcohol—PRISORINE 3515 (HBSP 17.9) ex UNIQEMA;

branched liquid fatty acids, particularly isostearic acid and dimer acid (dimerised fatty acids, particularly oleic and/or linoleic acids), such as dilinoleic acid (HBSP 17.8); and paraffinic oils, especially branched paraffinic oils e.g. ARLAMOL HD—an iso-paraffinic oil (HBSP 15.6) ex UNIQEMA;

silicone oils, which may be volatile or non-volatile, particularly dimethylpolysiloxane oils (dimethicone oils), including cyclomethicone oils, and silicone oils with non-methyl substituents as in phenyl trimethicone.

The oils, particularly the above oils can be used as mixtures of two or more different types of oils e.g. mixtures of silicone oils and ester oils.

The amount of the structurant included in oil based formulations will depend on the desired effect, but will usually be in the range from 0.1 to 20% by weight, more usually from 0.2 to 15%, particularly from 0.5 to 10% by weight and especially from 0.5 to 5 or 7% by weight, of the formulation.

The compounds of and used in this invention may be used alone or, if desired in combination with other structurants, particularly to ensure that the desired structuring effect it achieved the entire temperature range required for a particular product when used with other structurants, the proportion of structurant of the invention will generally be from 25 to 95%, more usually from 40 to 80%, by weight of the total structurant used. The total amount of structurant when mixtures are used will generally be within the ranges given above for the compounds of the invention.

The structurants will generally be incorporated into the oil based formulations by dissolving the structurant in the oil, usually at moderately elevated temperature typically from 50 to 90° C., more usually from 60 to 85° C., commonly at about 80° C., and then cooling the mixture or allowing the mixture to cool to ambient temperature. The structuring effects become apparent on cooling.

The compounds of and used in the invention are useful as structurants in oil based systems, in particular in personal care formulations. The desirable effects that they will be used to provide may include: increased viscosity ranging from modest thickening to true gelling which can be useful in making anhydrous gels which can protect moisture and/or to oxygen sensitive formulation components; modifying the rheological profile, to alter formulation delivery or spreading, or to provide improved colour or UV protection; improved surface adhesion, giving better wear or water resistance or non-transfer properties; modified tactile sensory properties giving reduced perceived oiliness or to create an impression of softness; or improved formulation stability by reducing or preventing separation, sedimentation or syneresis. The physical form of such personal care formulations includes dispersions of cosmetic materials e.g. pigments, sunscreen components or other active materials in oil based formulations; in water in oil emulsions e.g. skin creams; or in oil in water formulations to reduce perceived oiliness after application particularly after the water continuous phase evaporates from or is absorbed into the skin. The types of personal care product to which this technology is applicable include decorative cosmetics such as stick formulations such as lipstick, eyeliner and concealer, mascara, cosmetic foundation and cream powders; antiperspirant and deodorant products, particularly sticks and gels; baby oils (particularly based on paraffinic oils) and other skin care oil mixtures including hair, massage, make up remover and cleansing products; shampoos, particularly where a relatively viscous carrier material is desired; stick formulations such as lip balm and anti-acne sticks; and sun care products, particularly sunscreens e.g. those based in whole or in part on ultrafine pigments such as titanium dioxide or zinc oxide or similar materials. The amount of the structurant included in such personal care formulations will generally be within the ranges given above and other structurants may be included if desired also as described above.

Other end uses of the compounds of the invention include as structurants in oil based crop protection formulations, particularly so-called oil flowable formulations; and as structurants in greases.

The following examples illustrate the invention. All parts and percentages are molar unless otherwise stated.

Materials

Pol1 glycerol
Pol2 sorbitol
DA1 adipic acid
DA2 sebacic acid
FA1 stearic acid
FA2 behenic acid
FA3 palmitic acid/stearic acid blend 1:1 by mol
Cat1 potassium carbonate
Cat2 a mixture of $H_3PO_3$ and NaOH in a molar ratio of 1.59:4.0
Cat3 p-toluene sulphonic acid
Cat4 $H_3PO_3$
Cat5 NaOH
Cat6 KOH
Oil1 stearyl alcohol 15-polypropoxylate—ARLAMOL E ex UNIQEMA
Oil2 castor oil
Oil3 isostearyl alcohol—PRISORINE 3515 ex UNIQEMA
Oil4 glycerol tris-2-ethylhexanoate ester oil—ESTOL 3609 ex UNIQEMA
Oil5 glycerol triisostearate—PRISORINE 2041 ex UNIQEMA Oil6 trimethylolpropane triisostearate—PRISORINE 3630 ex UNIQEMA Oil7 C12/15 benzoate ester mixture—FINSOLVE TN ex FINETEX Inc Oil8 methyl oleate—PRIOLUBE 1400 ex UNIQEMA Oil9 isopropyl isostearate—PRISORINE 2021 ex UNIQEMA Oil10 isohexadecane emollient oil—ARLAMOL HD ex UNIQEMA Oil11 1:1 by wt blend of cyclomethicone and Oil2

Oil12 phenyl trimethicone

Test Methods

Acid Value—was measured using ASTM D1980-87 and quoted as "AV" in mg(KOH).g$^{-1}$.

Hydroxyl No—was measured using ASTM D1957-88 and quoted as "OH" in mg(KOH).g$^{-1}$. ["Free OH" no is OH-AV.]

Viscosity was measured on a solution of structurant generally at 5 wt % (a few were done at 10 wt %) in the test oil in a Brookfield DV1+ viscometer generally at 10 rpm (a few were measured at 5 rpm as indicted with the data) using T bar S95, with the measurement being made 1 minute after starting rotating the T bar, and the results are quoted in Pa·s.

Melting Points (MP in ° C.) were measured on fine powder samples of polymer (ground to in a mortar) on a Gallenkamp capillary melting point stage at heat setting 1 and reported as the temperature at which the product became a clear melt.

Molecular Weight was measured by gel permeation chromatography on a Viscotek Evolution GPC system using a mixed gel column and THF eluent against polystyrene standards. The results enabled both number and weight average molecular weights to be calculated.

SYNTHESIS EXAMPLES

Synthesis Example SE1

Poly(sorbitol sebacate)behenate

Anhydrous polyol P2 (36.4 g; 0.2 mol), dicarboxylic acid DA2 (32.3 g; 0.16 mol), monocarboxylic fatty acid FA2 (136.1 g; 0.4 mol), catalyst Cat2 [H$_3$PO$_3$ (0.26 g; 1.59 mol % on polyol) and NaOH (0.64 g 50% aqueous solution; 4 mol % on polyol)] were charged to a 250 ml round bottomed flask fitted with a propeller stirrer, side-arm water condenser and collection flask, nitrogen sparge thermometer (thermocouple) and isomantle. The mixture was heated under stirring (300 rpm) to 240° C. under nitrogen sparge removing water of reaction through the condenser. The reaction was monitored by acid value and stopped when the acid value was less than 10 (after 5 to 6 hrs) and the product discharged. The measured molecular weight was Mn 3670; Mw 14700 and MP 64° C.

Synthesis Example SE2

Poly(sorbitol sebacate)behenate

Anhydrous P2 (32.76 g; 0.18 mol), DA2 (18.18 g; 0.09 mol), FA2 (91.80 g; 0.27 mol) and Cat1 (1.86 g; 7.5 mol % based on polyol) were charged to a reaction vessel as described in SE1 and the mixture heated with stirring (300 rpm) to 170° C. under nitrogen sparge and at a vacuum of 100 mbar (gauge). The reaction was monitored by acid value and stopped when this fell below 20 (after 4 to 5 hrs) and the product discharged. The measured molecular weight was Mn 1480; Mw 3220.

Synthesis Example SE3

Poly(glycerol sebacate)behenate

P1 (100.0 g; 1.09 mol), DA2 (175.6.2 g; 0.87 mol), FA2 (369.6 g; 1.09 mol) and Cat3 (0.89 g; 1 mol % on polyol) were charged to a 1 l round bottomed flask fitted as described in SE1 and the mixture heated with stirring (300 rpm) to 220° C. under nitrogen sparge. The reaction was stopped when the acid value fell below 5 (after 4 to 5 hrs) and the product discharged.

Further oligo-(sorbitol and glycerol ester) esters were made by the general methods set out in Syntheses Examples SE1 to SE3 but making appropriate changes to the materials, proportions or conditions. The product of Synthesis Example SE9 has a high OH no with hydroxyl group loss minimised by using a relatively large amount of alkali catalyst, avoiding acid catalyst, using a modest proportion of monocarboxylic acid and avoiding very high reaction temperatures.

The products made in the Synthesis Examples and the reaction conditions used are summarised in Table 1 below. Amounts of polyol diacid and fatty acid are molar proportions (based on polyol=1) and of catalyst are mole percent (based on polyol).

TABLE 1

| Lab Ref | Ex No | polyol type | amt | diacid type | amt | monoacid type | amt | catalyst type | amt | temp (° C.) | press (mbar) | time (h) | AV | OH | MP |
|---|---|---|---|---|---|---|---|---|---|---|---|---|---|---|---|
| 20625/59 | SE1 | Pol2 | 1 | DA2 | 0.8 | FA2 | 2.0 | Cat2 | 1.59* | 240 | atm | 5.5 | 5.0 | — | 64 |
| 20625/47 | SE2 | Pol2 | 1 | DA2 | 0.5 | FA2 | 1.5 | Cat1 | 7.5 | 170 | 100 | 5 | 18.5 | — | — |
| 20631/12 | SE3 | Pol1 | 1 | DA2 | 0.8 | FA2 | 1.0 | Cat4 | 1.0 | 220 | atm | 5.5 | 6.0 | — | — |
| 20581/112 | SE4 | Pol2 | 1 | DA2 | 0.6 | FA3 | 1.5 | Cat1 | 7.5 | 170 | 100 | 10 | 4.3 | — | 60 |
| 20581/119 | SE5 | Pol1 | 1 | DA1 | 0.6 | FA2 | 1.0 | Cat6 | 7.5 | 200 | 100 | 3.5 | 15.3 | — | — |
| 20520/112 | SE6 | Pol2 | 1 | DA2 | 0.6 | FA2 | 1.8 | Cat2 | 1.59* | 240 | atm | 4 | 3.6 | 14.5 | — |
| 20581/111 | SE7 | Pol1 | 1 | DA1 | 0.6 | FA1 | 1.0 | Cat3 | 1.0 | 170 | 100 | 3.5 | 6.4 | — | — |
| 20520/111 | SE8 | Pol1 | 1 | DA2 | 0.6 | FA2 | 1.2 | Cat3 | 1.0 | 170 | 100 | 3.5 | 5.1 | 16.2 | 71 |
| 20648/17 | SE9 | Pol2 | 1 | DA2 | 0.5 | FA2 | 1.5 | Cat5 | 15.0 | 210 | atm | 4.5 | 9.8 | 205.0 | 78 |
| 20625/24 | SE10 | Pol2 | 1 | DA2 | 0.6 | FA2 | 1.3 | Cat1 | 7.5 | 170 | 100 | 9.5 | 4.8 | — | — |
| 20625/85 | SE11 | Pol1 | 1 | DA2 | 0.6 | FA2 | 1.2 | Cat2 | 1.59* | 240 | atm | 4.5 | 3.8 | — | 67 |
| 20625/70 | SE12 | Pol1 | 1 | DA2 | 0.6 | FA2 | 1.2 | Cat4 | 1.0 | 220 | 100 | 6.5 | 2.8 | 69.5 | 67 |
| 20625/81 | SE13 | Pol1 | 1 | DA2 | 0.5 | FA2 | 1.0 | Cat4 | 1.0 | 220 | atm | 4.0 | 1.1 | 85.0 | 66 |

*amount mol % of H$_3$PO$_3$ component of catalyst based on polyol

Application Examples AE1 to AE13

Test formulations were made by dissolving the polymers of Synthesis Examples SE1 to SE13 in various oils by heating a mixture of oil and structurant to 80° C. under moderate stirring and allowing the mixture to cool to ambient temperature once the structurant had dissolved. Generally 5% by weight polymer on the combined polymer and oil was used. The viscosity of the oils was measured the day following make up of the structured oil and the results are set out in Table 2 below.

TABLE 2

| Lab Ref | Ex No | polymer type | Viscosity (Pa·s) | | | | | | | | | | | |
|---|---|---|---|---|---|---|---|---|---|---|---|---|---|---|
| | | | Oil1 | Oil2 | Oil3 | Oil4 | Oil5 | Oil6 | Oil7 | Oil8 | Oil9 | Oil10 | Oil11 | Oil12 |
| 20625/59 | AE1 | SE1 | 205 | 278 | 245 | 472 | 237 | >500 | 156 | 112 | 134 | 30 | 272 | 9 |
| 20625/47 | AE2 | SE2 | 68 | — | 99.5 | 54 | — | — | 73 | 55 | 55.5 | 2.5 | — | — |
| 20631/12 | AE3 | SE3 | 83.5 | 189 | 81 | 41.5 | 82 | 87 | 33.5 | — | 16.5 | 25.5 | 46 | — |
| 20581/112 | AE4[2] | SE4 | 8.3[1] | — | 7.5[1] | 167[1] | — | — | 32.5 | — | 28.3[1] | 6.6[1] | — | — |
| 20581/119 | AE5[2] | SE5 | 51.6 | — | 26.6 | 1.6 | — | — | 3.3 | — | 3.3 | 6.6 | — | — |
| 20520/112 | AE6[2] | SE6 | 111 | — | 107 | 266 | — | — | 40 | 56.5 | 44 | 0.136 | — | — |
| 20581/111 | AE7[2] | SE7 | 50 | — | 19.2 | 14.2 | — | — | 0.017 | — | [3] | 15.8 | — | — |
| 20520/111 | AE8[2] | SE8 | 103 | — | 96.7 | 166 | — | — | 42.5 | 12.5 | 90 | 40 | — | — |
| 20646/17 | AE9 | SE9 | 65 | 123 | 46 | 57 | >500 | 140 | | 27 | 27 | 47 | 47 | |
| 20625/24 | AE10 | SE10 | 46.5 | 158 | 59 | 47 | 150 | 139 | 47.5 | 18 | 33 | <1 | — | — |
| 20625/85 | AE11 | SE11 | 54 | — | 60 | 100 | — | — | 4.5 | 26 | 34.5 | 9.5 | 68.5 | 45 |
| 20625/70 | AE12 | SE12 | 59 | 125 | 73 | 135 | 68 | 41 | 15 | 37.5 | 36 | 9 | — | — |
| 20625/81 | AE13 | SE13 | 81.5 | 143 | 72.5 | 52.5 | 45 | 48 | 9 | 32.5 | 40.5 | 20.5 | — | — |

[1] using 10 wt % solution of structurant
[2] viscosity measured at 5 rpm
[3] product of SE7 too insoluble in Oil9 to make up test solution

The invention claimed is:

1. A polyester oil structurant compound obtainable by the reaction of:
   i) a polyol;
   ii) a $C_4$ to $C_{10}$ dicarboxylic acid; and
   iii) a $C_{16}$ to $C_{30}$ monocarboxylic fatty acid;
   wherein:
   i) the molar ratio of the polyol:dicarboxylic acid:monocarboxylic fatty acid used in the reaction is 1:0.5-0.95:1-2.5; and
   ii) the polyester oil structurant compound has a hydroxyl number of 15 to 250 mg(KOH)g$^{-1}$, a number average molecular weight of 1,000 to 10,000, and a weight average molecular weight of from 2,500 to 20,000.

2. The structurant compound of claim 1, wherein the polyol has an average of from 1 to 2 primary hydroxyl groups and at least one secondary hydroxyl group(s).

3. The structurant compound of claim 2, wherein the polyol is glycerol, sorbitol, sorbitan or a mixture or combination of these.

4. The structurant compound of claim 1, wherein the dicarboxylic acid is of the formula HOOC—$R^2$—COOH (II), where $R^2$ is a $C_2$ to $C_8$ hydrocarbyl group.

5. The structurant compound of claim 4, wherein $R^2$ is a group —$(CH_2)_{m^-}$, where m is from 2 to 8.

6. The structurant compound of claim 1, wherein the monocarboxylic fatty acid is a $C_{18}$ to $C_{30}$ fatty acid.

7. The structurant compound of claim 6, wherein the monocarboxylic fatty acid is behenic acid.

8. A structured oil, comprising an oil and the structurant compound of claim 1.

9. The structured oil of claim 8, wherein the oil is one or more of a fatty alcohol polyalkoxylate, an ester oil, an aromatic ester oil, a branched liquid fatty alcohol, a branched liquid fatty acid, a paraffinic oil, and/or a silicone oil.

10. The structured oil of claim 8, wherein the structured oil comprises from 0.1 to 10% by weight of the structurant compound.

11. A personal care product, comprising the structured oil of claim 1.

12. The personal care product of claim 11, wherein the personal care product is in the form of an oil based formulation, a water in oil emulsion or an oil in water emulsion.

13. The personal care product of claim 11, wherein the personal care product is: a lipstick; an eyeliner; a concealer; a mascara; a cosmetic foundation or a cream powder; an antiperspirant and deodorant stick or gel; a baby oil; a hair oil; a massage oil; a makeup remover or cleansing product; a shampoo; a sun care product, a lip balm; or an anti-acne stick.

14. The structurant compound of claim 1, wherein the polyester oil structurant compound has an acid value of less than 5 mg(KOH)g$^{-1}$.

15. The structurant compound of claim 1, wherein the polyester oil structurant compound has an acid value of less than 10 mg(KOH)g$^{-1}$.

16. The structurant compound of claim 1, wherein the polyester oil structurant compound has an acid value of up to 20 mg(KOH)g$^{-1}$.

17. The structurant compound of claim 1, wherein the polyester oil structurant compound has a molar ratio of OH:COOH groups of at least 1.3, based on amounts of these functional groups in the starting material reactants.

18. The structurant compound of claim 1, wherein the reaction employs a molar ratio of 1:0.5-0.85:1-2.5 of the polyol, the dicarboxylic acid, and the monocarboxylic fatty acid, respectively.

19. The structurant compound of claim 1, wherein the polyester oil structurant compound has a number average molecular weight of 1,200 to 7,000 and a weight average molecular weight of from 2,500 to 12,000.

20. A method of increasing viscosity of an oil or an oil phase of an oil based system or formulation, comprising:
   introducing 0.1-20 wt. % of the polyester oil structurant compound of claim 1 into the oil or oil phase of the oil based system or formulation.

21. The method of claim 20, wherein the oil or oil phase of the oil based system or formulation has a Hansen and Beerbower value of 15 to 25.

22. The method of claim 20, wherein the oil based system or formulation is a water in oil emulsion or an oil in water emulsion.

23. The method of claim 20, wherein the oil based system or formulation is a personal care formulation or personal care product.

\* \* \* \* \*